(12) United States Patent
Rieping et al.

(10) Patent No.: US 6,184,006 B1
(45) Date of Patent: Feb. 6, 2001

(54) METHOD FOR THE FERMENTATIVE PRODUCTION OF D-PANTOTHENIC ACID USING STRAINS OF THE FAMILY ENTEROBACTERIACEAE

(75) Inventors: Mechthild Rieping; Georg Thierbach, both of Bielefeld; Walter Pfefferle, Halle; Nicole Dusch, Bielefeld; Jorn Kalinowski, Bielefeld; Alfred Puhler, Bielefeld, all of (DE)

(73) Assignee: Degussa-Hüls Aktiengesellschaft, Hanau (DE)

( * ) Notice: Under 35 U.S.C. 154(b), the term of this patent shall be extended for 0 days.

(21) Appl. No.: 09/318,739

(22) Filed: May 26, 1999

(30) Foreign Application Priority Data

Dec. 1, 1998 (DE) ............................. 198 55 314

(51) Int. Cl.⁷ .................................................. C12P 13/00
(52) U.S. Cl. ...................................... 435/128; 435/252.33
(58) Field of Search ............................... 435/128, 252.33

(56) References Cited

U.S. PATENT DOCUMENTS 5,518,906 * 5/1996 Hikichi et al. ........................ 435/116

FOREIGN PATENT DOCUMENTS 0 493 060 A2 * 7/1992 (EP) ................................ C12P/13/02

OTHER PUBLICATIONS

Weickert et al. Optimization of heterologous protein production in *Escherichia coli*. Current Opinion in Biotechnology (1996) 7:494–499, 1996.*

Cronan et al. Genetic and Biochemical Analyses of Pantothenate Biosynthesis in *Escherichia coli* and *Salmonella typhimurium*. Journal of Bacteriology. (1982) 149,3: 916–922, 1982.*

Merkel et al. Nucleotide sequence of the *Escherichia coli* panBCD gene cluster. (1993) GenBank accession number L17086, 1993.*

* cited by examiner

*Primary Examiner*—Ponnathapu Achutamurthy
*Assistant Examiner*—Kathleen Kerr
(74) *Attorney, Agent, or Firm*—Pillsbury Madison & Sutro LLP

(57) ABSTRACT

A method for the production of D-pantothenic acid by the fermentation of microorganisms of the family Enterobacteriacae producing D-pantothenic acid which is characterized in that strains are used which
  a) Contain the plasmid pFV31 and/or pFV202 and that
  b) A panD gene and optionally other nucleotide sequences coding for aspartate-1-decarboxylase are enhanced, especially overexpressed in these microorganisms,
  c) The pantothenic acid is enriched in the medium or in the cells of the microorganisms and
  d) The pantothenic acid formed is isolated.

5 Claims, 2 Drawing Sheets

SEQUENCE LISTING

<160> NUMBER OF SEQ ID NOS: 6

<210> SEQ ID NO 1
<211> LENGTH: 540
<212> TYPE: DNA
<213> ORGANISM: Corynebacterium glutamicum
<220> FEATURE:
<221> NAME/KEY: CDS
<222> LOCATION: (77)..(484)

<400> SEQUENCE: 1

```
aatattcctt tccttgtcat ctcacgctat gatttctaaa acttgcagga caaccccccat       60 aaggacacca caggac atg ctg cgc acc atc ctc gga agt aag att cac cga      112
               Met Leu Arg Thr Ile Leu Gly Ser Lys Ile His Arg
                 1               5                  10 gcc act gtc act caa gct gat cta gat tat gtt ggc tct gta acc atc        160
Ala Thr Val Thr Gln Ala Asp Leu Asp Tyr Val Gly Ser Val Thr Ile
         15                  20                  25 gac gcc gac ctg gtt cac gcc gcc gga ttg atc gaa ggc gaa aaa gtt        208
Asp Ala Asp Leu Val His Ala Ala Gly Leu Ile Glu Gly Glu Lys Val
     30                  35                  40 gcc atc gta gac atc acc aac ggc gct cgt ctg gaa act tat gtc att        256
Ala Ile Val Asp Ile Thr Asn Gly Ala Arg Leu Glu Thr Tyr Val Ile
 45                  50                  55                  60 gtg ggc gac gcc gga acg ggc aat att tgc atc aat ggt gcc gct gca        304
Val Gly Asp Ala Gly Thr Gly Asn Ile Cys Ile Asn Gly Ala Ala Ala
                 65                  70                  75 cac ctt att aat cct ggc gat ctt gtg atc atc atg agc tac ctt cag        352
His Leu Ile Asn Pro Gly Asp Leu Val Ile Ile Met Ser Tyr Leu Gln
             80                  85                  90 gca act gat gcg gaa gcc aag gcg tat gag cca aag att gtg cac gtg        400
Ala Thr Asp Ala Glu Ala Lys Ala Tyr Glu Pro Lys Ile Val His Val
         95                 100                 105 gac gcc gac aac cgc atc gtt gcg ctc ggc aac gat ctt gcg gaa gca        448
Asp Ala Asp Asn Arg Ile Val Ala Leu Gly Asn Asp Leu Ala Glu Ala
     110                 115                 120 cta cct gga tcc ggg ctt ttg acg tcg aga agc att tagcgtttta            494
Leu Pro Gly Ser Gly Leu Leu Thr Ser Arg Ser Ile
125                 130                 135 gctcgccaat attgctgccg gcctcgttga aaatggtcat ggtggc                     540
```

<210> SEQ ID NO 2
<211> LENGTH: 136
<212> TYPE: PRT
<213> ORGANISM: Corynebacterium glutamicum

<400> SEQUENCE: 2

```
Met Leu Arg Thr Ile Leu Gly Ser Lys Ile His Arg Ala Thr Val Thr
  1               5                  10                  15

Gln Ala Asp Leu Asp Tyr Val Gly Ser Val Thr Ile Asp Ala Asp Leu
             20                  25                  30

Val His Ala Ala Gly Leu Ile Glu Gly Glu Lys Val Ala Ile Val Asp
         35                  40                  45
```

-continued

```
Ile Thr Asn Gly Ala Arg Leu Glu Thr Tyr Val Ile Val Gly Asp Ala
    50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                85                  90                  95

Glu Ala Lys Ala Tyr Glu Pro Lys Ile Val His Val Asp Ala Asp Asn
                100                 105                 110

Arg Ile Val Ala Leu Gly Asn Asp Leu Ala Glu Ala Leu Pro Gly Ser
            115                 120                 125

Gly Leu Leu Thr Ser Arg Ser Ile
    130                 135
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
gaattcgaca gggtagaaag gtaga                                       25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
agatctggga taacaatcaa gcaacc                                      26

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
catctcacgc tatgaattct                                             20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
acgaggcctg cagcaata                                               18

METHOD FOR THE FERMENTATIVE PRODUCTION OF D-PANTOTHENIC ACID USING STRAINS OF THE FAMILY ENTEROBACTERIACEAE

BACKGROUND INFORMATION

Pantothenic acid is a commercially significant vitamin which is used in cosmetics, medicine, human nourishment and in animal nourishment.

Pantothenic acid can be produced by chemical synthesis or biotechnologically by the fermentation of suitable microorganisms in suitable nutrient solutions. DL-pantolactone is an important intermediate stage in the chemical synthesis. It is produced in a multi-stage process from formaldehyde, isobutylaldehyde and cyanide. In further method steps the racemic mixture is separated and D-pantolactone condensed with β-alanine and D-pantothenic acid obtained. The advantage of the fermentative production with microorganisms resides in the direct formation of the desired D-form of pantothenic acid, which is free of L-pantothenic acid.

Various types of bacteria such as, for example, *Escherichia coli, Arthrobacter ureafaciens, Corynebacterium erythrogenes, Brevibacterium ammoniagenes* and also yeasts such as, for example, *Debaromyces castellii* can produce D-pantothenic acid in a nutrient solution containing glucose, DL-pantoic acid and β-alanine, as is shown in EP-A 0,493,060. EP-A 0,493,060 also shows that the formation of D-pantothenic acid is improved in the case of *Escherichia coli* by amplification of pantothenic-acid biosynthetic genes, which are contained on the plasmids pFV3 and pFV5, in a nutrient solution containing glucose, DL-pantoic acid and β-alanine.

EP-A 0,590,857 and U.S. Pat. No. 5,518,906 are relative to mutants derived from *Escherichia coli* strain IFO3547 such as FV5714, FV525, FV814, FV521, FV221, FV6051 and FV5069 which carry resistance genes against various antimetabolites such as salicylic acid, (α-ketobutyric acid, β-hydroxyaspartic acid, O-methylthreonine and α-ketoisovaleric acid and produce D-pantothenic acid in a nutrient solution containing glucose, pantoic acid and in a nutrient solution containing glucose and β-alanine.

E-A 0,590,857 also shows that after the amplification of general pantothenic-acid biosynthesis genes contained on the plasmid pFV31, in the strains cited above, the production of D-pantoic acid is improved in a nutrient solution containing glucose and that the production of D-pantothenic acid is improved in a nutrient solution containing glucose and β-alanine.

Moreover, WO97/10340 shows that after increasing the activity of the enzyme acetohydroxy-acid synthase II by amplification of the ilvGM gene by means of plasmid pFV202, an enzyme of valine biosynthesis, the production of D-pantoic acid is improved in a nutrient solution containing glucose and that the production of D-pantothenic acid is improved in a nutrient solution containing glucose and β-alanine.

It can not be gathered from the texts cited to what extent the cited strains produce pantothenic acid in a nutrient solution containing solely glucose or solely saccharose as substrate.

SUMMARY OF THE INVENTION

The present inventors had the objective of further improving strains of the family Enterobacteriaceae, especially of the genus Escherichia, which form pantothenic acid.

Pantothenic acid, or vitamin B, is a commercially significant product which is used in cosmetics, medicine, human nourishment and in animal nourishment. There is therefore general interest in making available improved methods of producing pantothenic acid.

When D-pantothenic acid or pantothenic acid or pantothenate are mentioned in the following text not only the free acid but also the salts of D-pantothenic acid such as, for example, the calcium salt, sodium salt, ammonium salt or potassium salt are included.

Subject matter of the invention is constituted by a method of producing D-pantothenic acid by fermentation of microorganisms of the family Enterobacteriaceae, especially of the genus Escherichia, which produce D-pantothenic acid, which method is characterized in that the microorganisms a) Contain the plasmid pFV31 and/or pFV202, preferably pFV31, and in which b) The panD gene and optionally other nucleotide sequences coding for aspartate-1-decarboxylase (E.C. 4.1.1.11) are enhanced, preferably overexpressed.

It is preferable to use microorganisms with DNA whose nucleotide sequence codes for panD with an origin from *E. coli*, and also from coryneform bacteria. A replicative DNA is preferable, in which (i) The nucleotide sequence, shown in SEQ ID NO:1, codes for panD, or (ii) The latter corresponds to sequence (i) within the range of the degeneration of the genetic code, or (iii) The latter hybridizes with a sequence complementary to sequence (i) or (ii) and, optionally, (iiii) The latter carries functionally neutral sense mutations in (i).

The fermentation preferably takes place in a nutrient solution which exclusively contains glucose or saccharose as substrate and is free of β-alanine and pantoic acid.

The production of pantothenic acid is improved in this manner in accordance with the invention. The addition of aspartate, β-alanine, ketoisovalerate, ketopantoic acid or pantoic acid and/or their salts is desired if necessary.

The concept "enhancement" describes in this connection the elevation of the intracellular activity of one or several enzymes in a microorganism which are coded by the corresponding DNA in that, for example, the copy number of the gene(s) is increased, a strong promoter is used or a gene is used which codes for a corresponding enzyme with a high activity and optionally combines these measures.

The microorganisms constituting the subject matter of the present invention can produce pantothenic acid from glucose, saccharose, lactose, fructose, maltose, molasses, starch, cellulose or from glycerol and ethanol. Glucose or saccharose is preferably used. This includes, in particular, Gram-negative bacteria such as, for example, those of the family Enterobacteriaceae. In the latter, the genus Escherichia with the species *Escherichia coli* is to be cited in particular. Within the species *Escherichia coli* the so-called K-12 strains such as, for example, the strains MG1655 or W3110 (Neidhard et al.: *Escherichia coli* and Salmonella. Cellular and Molecular Biology (ASM Press, Washington, D.C.)) or the *Escherichia coli* wild-type strain IFO3547 (Institute for Fermentation, Osaka, Japan) and mutants derived from them that have the capacity of producing pantothenic acid are suitable. Note in particular in this connection the strains 3547/pFV31, 5714/pFV31, 525/pFV31, 814/pFV31, 521/pFV31, FV221/pFV31, FV6051/pFV31, FV5069/pFV31, FV5069/pFV202 and those which are produced from the latter by conventional mutagenesis, selection, for example, for antimetabolic resistance such as azidothymidine resistance, thiaisoleucine resistance and screening. The strains FV5069/pFV31 and FV5069/pFV202 deposited as FERM BP 4395 and FERM BP 5227 in accordance with the Budapest Convention are especially suitable (see EP-A 0,590,857 and WO 97/10340).

In order to achieve an enhancement, especially an overexpression, for example, the copy number of the corresponding genes is elevated or the promoter and regulation region, which is located upstream from the structural gene, is mutated. Expression cassettes which are inserted upstream from the structural gene operate in the same manner. It is additionally possible to increase the expression in the course of the fermentative formation of D-pantothenate by inducible promoters. The expression is also improved by measures for extending the life of m-RNA. Furthermore, the enzymatic activity is enhanced by preventing the degradation of the enzymatic protein. The genes or gene constructs can be present either in plasmids with different copy number or be integrated in the chromosome and amplified. Alternatively, an overexpression of the genes concerned can be achieved by altering the composition of the media and conduction of the culture.

A skilled artisan will find instructions for this in, among others, Chang and Cohen (Journal of Bacteriology 134: 1141–1156 (1978)), in Hartley and Gregori (Gene 13: 347–353 (1981)), in Amann and Brosius (Gene 40: 183–190 (1985)), in de Broer et al., (Proceedings of the National [Academy] of Sciences of the United States of America 80: 21–25 (1983), in LaVallie et al. (BIO/TECHNOLOGY 11, 187–193 (1993)), in PCT/US97/13359, in Llosa et al. (Plasmid 26: 222–224 (1991)), in Quandt and Klipp (Gene 80: 161–169 (1989)), in Hamilton (Journal of Bacteriology 171: 4617–4622 (1989)), in Jensen and Hammer (Biotechnology and Bioengineering 58, 191–195 (1998)) and in standard textbooks of genetics and molecular biology.

The panD gene of *E. coli* is known. The nucleotide sequence was published by Merkels and Nichols (FEMS Microbiology Letters 143, 247–252 (1996)). A PCR (polymerase chain reaction) method, like the generally known one, or one of the methods cited below can be used to isolate or produce the panD gene of *E. coli*.

In order to isolate the panD gene from *C. glutamicum*, first a gene bank of this microorganism is established in *E. coli*. The establishment of gene banks is documented in standard textbooks and manuals. The textbook of Winnacker: Gene und Klone, Eine Einführung in die Gentechnologie [German—Genes and Clones, An Introduction to Gene Technology] (Verlag Chemie, Weinheim, Germany, 1990) or the manual of Sambrook et al.: Molecular Cloning, A Laboratory Manual (Cold Spring Harbor Laboratory Press, 1989) are cited as examples. A known gene bank is that of the *E. coli* K-12 strain W3110 established by Kohara et al. (Cell 50, 495–508 (1987)) in λ vectors. Bathe et al. (Molecular and General Genetics, 252:255–265, 1996) describe a gene bank of *C. glutamicum* ATCC13032 which was established with the aid of the cosmid vector SuperCos I (Wahl et al., 1987, Proceedings of the National Academy of Sciences USA, 84:2160–2164) in the *E.coli* strain K-12 NM554 (Raleigh et al., 1988, Nucleic Acids Research 16:1563–1575). In order to produce a gene bank of *C. glutamicum* in *E. coli*, plasmids such as pBR322 (Bolivar, Life Sciences, 25, 807–818 (1979)) or pUC9 (Vieira et al., 1982, Gene 25: 259–268) can be used. Suitable hosts are especially those *E. coli* strains which are restriction-defective and recombination-defective. An example for this is the strain DH5αmcr described by Grant et al., (Proceedings of the National Academy of Sciences USA, 87 (1990) 4645–4649). The gene bank is subsequently inserted into an indicator strain by transformation (Hanahan, Journal of Molecular Biology 166, 557–580, 1983) or electroporation (Tauch et al., 1994, FEMS Microbiological Letters, 123:343–347). The indicator strain is distinguished in that it comprises a mutation in the gene under consideration which causes a detectable phenotype, for example, an auxotrophy. In the framework of the present invention the *E. coli* mutant DV9 (Vallari and Rock, Journal of Bacteriology 1985, 164:136–142), which carries a mutation in the panD gene, is especially interesting.

After transformation of the indicator strain such as, for example, the panD mutant DV9 with a recombinant plasmid carrying the gene being considered, such as, for example, the panD gene, and expression of the same the indicator strain becomes prototrophic relative to the corresponding quality such as, for example, the need for pantothenic acid.

The gene or DNA fragment isolated in this manner can be described and characterized by determination of the sequence as described, for example, in Sanger et al., (Proceedings of the National Academy of Sciences of the United States of America USA, 74:5463–5467, 1977).

In this manner the novel DNA sequence of *C. glutamicum* coding for the gene panD was obtained, which is a component of the present invention as SEQ ID NO:1. Furthermore, the amino-acid sequences of the corresponding enzyme were derived from the present DNA sequence with the methods described above. The resulting amino-acid sequence of the panD gene product, namely, L-aspartate 1-decarboxylase, is shown in SEQ ID NO:2.

Coding DNA sequences resulting from SEQ ID NO:1 by the degeneracy of the genetic code are likewise components of the invention. In the same manner DNA sequences which hybridize with SEQ ID NO:1 are components of the invention. Furthermore, in the technical world conservative amino-acid exchanges such as, for example, the exchange of glycine for alanine or of aspartic acid for glutamic acid in proteins are known as sense mutations which do not result in any basic change of the activity of the protein, that is, they are functionally neutral. It is furthermore known that changes on the N- and/or C terminus of a protein do not significantly affect its function in an adverse manner or can even stabilize it.

An expert in the art will find data about this in, among other locations, Ben-Bassat et al., (Journal of Bacteriology 169:751–757 (1987)), in O'Regan et al., (Gene 77:237–251 (1989)), in Sahin-Toth et al., (Protein Sciences 3:240–247 (1994)), in Hochuli et al., (Bio/Technology 6:1321–1325 (1988)) and in standard textbooks of genetics and molecular biology.

The gene isolated and characterized in this manner can be subsequently expressed individually or in combination with others in suitable strains of *Escherichia coli*. A known method for expressing or overexpressing genes consists of amplifying them with the aid of plasmid vectors which can be provided in addition with expression signals. Those plasmid vectors which can replicate in the corresponding microorganisms can be considered for use as plasmid vectors. For *E. coli*, for example, the vectors pSC101 (Vocke and Bastia, Proceedings of the National Academy of Sciences USA 80 (21), 6557–6561 (1983)) or pKK223-3 (Brosius and Holy, Proceedings of the National Academy of Sciences USA 81, 6929 (1984)) or the *Corynebacterium glutamicum/Escherichia coli* shuttle vector pZ8-1 (European patent 0,375,889) can be considered for the present invention. Examples for such strains of *E. coli* are FV5069/pFV31/pND-D1 and FV5069/pFV31 pND-D2, which contain the plasmids pND-D1 and pND-D2. Plasmid pND-D1 is an *E. coli*-*C. glutamicum* shuttle vector which is based on the plasmid pZ8-1 and carries the panD gene of *E. coli*. Plasmid pND-D2 is an *E. coli*-*C. glutamicum* shuttle vector which is based on the plasmid pZ8-1 and carries the panD gene of *C. glutamicum*.

It is obvious to an expert in the art that chromosomal mutations which bring about resistances against metabolites and antimetabolites or which prevent the dissipation of precursors of pantothenic acid can be combined individually or in common in an advantageous manner with the measures constituting subject matter of the invention.

The microorganisms produced in accordance with the invention can be cultivated continuously or discontinuously in a batch method (batch cultivation) or in a feed batch method or repeated feed batch method for the purpose of producing pantothenic acid. A summary of known cultivation methods is described in the textbook by Chmiel (Bioprocesstechnik 1. Einführung in die Bioverfahrenstechnik [German—Bioprocessing Technology 1. Introduction to Bioengineering Technology] (Gustav Fischer Verlag, Stuttgart, 1991)) or in the textbook of Storhas (Bioreaktoren and periphere Einrichtungen [German—Bioreactors and Peripheral Apparatuses] (Vieweg Verlag, Braunschweig/Wiesbaden, 1994)).

The culture medium to be used must satisfy the demands of the particular microorganisms in a suitable manner. Descriptions of culture media of various microorganisms are contained in the manual "Manual of Methods for general Bacteriology" of the American Society for Bacteriology (Washington, D.C., USA, 1981). Sugars and carbohydrates such as, for example, glucose, saccharose, lactose, fructose, maltose, molasses, starch and cellulose, oils and fats such as, for example, soy oil, sunflower oil, peanut oil and coconut fat, fatty acids such as, for example, palmitic acid, stearic acid and lineic acid, alcohols such as, for example, glycerol and ethanol and organic acids such as, for example, acetic acid can be used as carbon source. These substances can be used individually or as a mixture. Organic, nitrogen-containing compounds such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate can be used as nitrogen source. The nitrogen sources can be used individually or as a mixture. Potassium dihydrogenphosphate or dipotassium hydrogenphosphate or the corresponding sodium-containing salts can be used as phosphorus source. The culture medium must also contain metal salts such as, for example, magnesium sulfate or iron sulfate, which are necessary for growth. Finally, essential growth substances such as amino acids and vitamins can be used in addition to the substances cited above. If desired, the precursors of pantothenic acid such as aspartate, β-alanine, ketoisovalerate or ketopantoic acid or pantoic acid and optionally their salts can be added to the culture medium. The cited substances to be used can be added to the culture in the form of a one-time batch or supplied in a suitable manner during the cultivation.

Basic compounds such as sodium hydroxide, potassium hydroxide, ammonia or acidic compounds such as phosphoric acid or sulfuric acid are added in a suitable manner for controlling the pH of the culture. Anti-foaming agents such as, for example, fatty-acid polyglycolester can be added for controlling the development of foam. In order to maintain the stability of plasmids, suitable, selectively acting substances, for example, antibiotics can be added to the medium. In order to maintain aerobic conditions, oxygen or oxygen-containing gas mixtures such as, for example, air are charged into the culture. The temperature of the culture is normally approximately 25° C. to 45° C. and preferably approximately 30° C. to 37° C. The culture is continued until a maximum of pantothenic acid has formed. This goal is normally achieved within 10 hours to 160 hours.

It is obvious to an expert in the art that strains which have a high activity of the enzyme L-aspartate 1-decarboxylase can also be used for the production of β-alanine from L-aspartate. For this the known fermentative methods, enzymatic conversion reactions or combinations of both are used.

The concentration of pantothenic acid formed can be determined with known methods (Velisek; Chromatographic Science 60, 515–560 (1992)).

The following microorganisms were deposited with the German Collection for Microorganisms and Cell Cultures (DSMZ, Braunschweig, Germany) Mascheroder Weg 1b, D38124 Braunschweig, Germany, on Oct. 5, 1998 in accordance with the Budapest Convention:

*Corynebacterium glutamicum* ATCC13032/pND-D2 as DSM12438

DETAILED DESCRIPTION OF THE INVENTION

The present invention is explained in detail in the following using exemplary embodiments.

EXAMPLE 1

Cloning, Sequencing of the panD gene of *C. glutamicum*

1. Cloning of the panD gene

Chromosomal DNA from *C. glutamicum* ATCC13032 was isolated as described in Tauch et al. (1995, Plasmid, 33:168–179) and partially cleaved with the restriction enzyme Sau3A (Pharmacia Biotech (Freiburg, Germany), product description Sau3A, code No. 27-0913-02). DNA fragments in a size range of 7–9 kb were isolated with the aid of the "Nucleotrap Extraction Kit for Nucleic Acids" (Macherey and Nagel, Düren, Germany; cat. No. 740584) and ligated into the dephosphorylated BamHI cleavage site of vector pUC19 (Norrander et al., 1982, Gene, 26:101-1–6), which was ordered from the company MBI Fermentas (Vilnius, Lithuania). The ligation was carried out as by Sambrook et al. (1989, Molecular Cloning: A Laboratory Manual, Cold Spring Harbor), during which the DNA mixture was incubated overnight with T4 ligase (Pharmacia Biotech, Freiburg, Germany). This ligation mixture was subsequently electroporated into the *E. coli* strain DH5αMCR (Grant, 1990, (Proceedings of the National Academy of Sciences USA, 87:4645–4649) (Tauch, 1994, FEMS Microbiological Letters, 123:343–347) and plated out onto LB agar (Lennox, 1955, Virology, 1:190)+100 µg/ml ampicillin. After incubation for 24 hours at 37° C. the *C. glutamicum* gene bank was able to be obtained from the transformants by re-isolation of the plasmid DNA according to the "alkaline lysis method" of Birnboim and Doly (Nucleic Acids Research, 7: 1513–1523, 1997). Competent cells of the *E. coli* strain DV9 (Vallari and Rock, 1985, Journal of Bacteriology, 164:136–142), which carries a mutation in the panD gene, were electroporated with this gene bank. The electroporation batch was washed twice following the regeneration phase (Tauch et al., 1994, FEMS Microbiological Letters, 123: 343–347) with medium E (Vogel and Bonner, 1956, Journal of Biological Chemistry, 218:97–106). The composition of medium E is shown in table 1. 50 ml medium E+100 µg/ml ampicillin, which were in a 250 ml Erlenmeyer flask, were inoculated with these cells and incubated in an air agitator at 250 U/min and 19°

C. After a two-day incubation the bacterial suspension was diluted and spread out onto LB agar (Lennox, 1955, Virology, 1:190) which had been supplemented with 100 µg/ml ampicillin.

TABLE 1

| Substance | Amount per liter | Comments |
|---|---|---|
| $K_2HPO_4$ | 10 g | |
| $NaNH_4HPO_4 * 4 H_2O$ | 3.5 g | |
| citric acid | 2 g | |
| $MgSO_4 * 7 H_2O$ | 0.2 g | |
| glucose | 4 g | sterilize separately |
| thiamin | 0.2 µg | sterilize by filtration |

The plasmid DNA of a DV9 transformant was isolated, designated as pNIC-1.3 and characterized by agarose gel electrophoresis (Sambrook et al.: Molecular Cloning, A Laboratory Manual 1989 Cold Spring Harbor Laboratory Press) and comparison with standard DNA fragments of a known length. Plasmid pNIC-1.3 contains an insertion with a length of 7 kbp. The complementation capacity of pNIC-1.3 was checked by renewed transformation of the panD mutant DV9. The transformants obtained were again capable of growing in medium E free of β-alanine under the conditions indicated above.

The subcloning of the 7 kb insert took place by cleaving the plasmid pNIC-1.3 with the restriction enzymes BamHI (Pharmacia Biotech (Freiburg, Germany), product description BamHI, code No. 27-0868-03), EcoRI (Pharmacia Biotech (Freiburg, Germany), product description EcoRI, code No. 27-0884-03) and BglII (Pharmacia Biotech (Freiburg, Germany), product description BglII, code No. 27-0946-02) and subsequent ligation into the appropriately restriction-digested vector pK18mob (Schäfer, 1994, Gene, 145:69–73). The ligation batch obtained was electroporated into the E. coli panD mutant DV9; the selection for complemented transformants took place as described above and the agar plates contained in this instance 50 µg/ml kanamycin. The plasmids of complemented individual clones were isolated and characterized by means of restriction analyses. An EcoRI subclone, called pNIC-10 in the following, with a DNA insert approximately 3 kb in size was selected for the following sequence analysis.

2. Sequencing of the panD gene

The 3 kb fragment of pNIC-10 was cleaved with various restriction enzymes for its double-stranded sequencing and the fragments subcloned into the plasmids pUC19 or pK18mob. The plasmid DNA used for the sequencing was isolated according to the instructions of the producer with the "QIAGEN Plasmid Mini Kit" (Qiagen, Inc., Chatsworth, Calif., USA) and the determination of the plasmid sizes carried out by agarose gel electrophoresis.

The sequencing took place according to the dideoxy chain-terminating method of Sanger et al. (Proceedings of the National Academies of Sciences USA, 74: 5463–5467, 1977) with modifications according to Zimmermann et al. (Nucleic Acids Research, 18:1067, 1990). The "Cy5-AutoRead Sequencing Kit" of Pharmacia (product NO. 27-2690-02, Freiburg, Germany) was used. The gel electrophoretic separation and analysis of the sequencing reaction took place in a LONG RANGER™ GEL SOLUTION polyacrylamide gel (FMC BioProducts, Rockland, Me., USA) with the "automatic Laser-Fluorescence (A.L.F.) Express DNA Sequencing Device" of Amersham Pharmacia Biotech (Uppsala, Sweden). The raw sequencing data obtained were subsequently processed using the Staden program packet (Nucleic Acids Research, 14:217–231, 1986) version 97-0. All individual sequences of the pNIC-10 clones were assembled to a cohesive contig 3060 bp in length which was designated as contig13. The computer-supported coding-range analysis with the program XNIP (Staden, 1986, Nucleic Acids Research, 14:217–231) of the entire DNA fragment resulted in the identification of five open reading frames (ORF's). FIG. 1 shows a restriction map of contig13 as well as the position of the ORF's designated as orf-1 to orf-5. Homology analyses were carried out with the "BLAST search programs" (Gish and States, 1993, Nature of Genetics, 3:266–272; Altschul et al., 1990, Journal of Molecular Biology, 215:403–410), which were made available via the online service of the NCBI server of the "National Library of Medicine" (Bethesda, Md., USA). The analysis of contig13 showed that orf-3 is the panD-gene. Orf-3 is designated in the following as panD. The nucleotide sequence of the DNA fragment carrying the panD gene is shown in SEQ ID NO:1. The amino-acid sequence of the panD gene product resulting with the above methods, namely, L-aspartate 1-decarboxylase, is shown in SEQ ID NO:2.

EXAMPLE 2

Construction of Vectors for the Expression of panD genes

The pantothenate biosynthesis gene panD from C. glutamicum and panD from E. coli were amplified using polymerase chain reaction (PCR) as well as synthetic oligonucleotides. The PCR experiments were carried out with the Taq DNA polymerase of the company Gibco-BRL (Eggestein, Germany) in a "PCT-100 Thermocycler" (MJ Research Inc., Watertown Mass., USA). A single denaturing step of 2 minutes at 94° C. was followed by a denaturing step of 90 seconds at 94° C., an annealing step for 90 seconds at a primer-dependent temperature of T=(2AT+4GC)−5° C. (Suggs et al., 1981, pp. 683–693, in: D. D. Brown and C. F. Fox (eds.), Developmental Biology Using Purified Genes, Academic Press, New York, USA) as well as a 90 second extension step at 72° C. The last three steps were repeated cyclically 35 times and the reaction terminated with a final extension step of 10 minutes at 72° C. The products amplified in this manner were ligated, after they had been tested electrophoretically in agarose gel, in accordance with the instructions of the producer into the vector pCR®2.1 (Original TA Cloning Kit, Invitrogene (Leek, Netherlands), product description Original TA Cloning® Kit, cat. No. KNM2030-01).) and subsequently transformed into the E. coli strain TOP10F'. The selection for transformants took place by incubation at 37° C. for 24 hours on LB agar plates with 100 µg/ml ampicillin and 40 µg/ml X-Gal (5-bromo-4-chloro-3-indolyl-β-D-galactoside).

Starting from the nucleotide sequences of the pantothenate biosynthesis gene panD from C. glutamicum ATCC 13032 (FIG. 2) and from E. coli K12 (W. K. Merkel and B. P. Nichols, 1993, GenBank: L17086), PCR primers were synthesized (MWG Biotech, Ebersberg, Germany). These primers were selected in such a manner that the amplified fragments contain the genes as well as their native ribosomal bonding sites but not possible promoter regions. In addition, suitable restriction cleavage sites were inserted which make possible the cloning into the target vector. The sequences of the PCR primers, the inserted cleavage sites (sequence underlined) as well as the amplified gene (fragment size in bp is indicated in brackets) are listed in Table 2.

TABLE 2

| Primer | Sequence with restriction cleavage site | | Product | Plasmid |
|---|---|---|---|---|
| panD-Ec1 | 5'-<u>GAATTC</u>GACAGGGTAGAAAGGTAGA-3'<br>     EcoRI | (SEQ ID NO:3) | $panD_{E.c.}$ | pND-D1 |
| panD-Ec2 | 5-<u>AGATCT</u>GGGATAACAATCAAGCAACC-3'<br>     BglII | (SEQ ID NO:4) | | |
| panD-Cg1 | 5-CATCTCACGCTAT<u>GAATTCT</u>-3'<br>             EcoRI | (SEQ ID NO:5) | $panD_{C.g.}$ | pND-D2 |
| panD-Cg2 | 5-ACGAGGC<u>CTGCAG</u>CAATA-3'<br>        PstI | (SEQ ID NO:6) | | |

The E. coli—C. glutamicum shuttle expression vector pZ8-1 (European patent 0.375,889) shown in FIG. 2 was used as base vector for the expression both in C. glutamicum as also in E. coli. The amplified $panD_{C.g.}$ cloned previously into vector pCR®2. 1 was ligated by means of the primer-inserted restriction cleavage sites into the expression vector pZ8-1 treated in the same manner and brought therewith under the control of the tac promoter contained on this plasmid. The amplified $panD_{E.c.}$ was cloned as EcoRI-BglII fragment into the compatible EcoRI-BamHI restriction ends of vector pZ8-1. The particular plasmid designations for the expression plasmids constructed in this manner are indicated in Table 2. The cloning strategy for the genes $panD_{E.c.}$ and $panD_{C.g.}$ is shown in FIG. 2. The correct cloning of the expression plasmids was tested by sequencing of the particular insert.

These plasmids pND-D1 and pND-D2 were transformed into the E. coli strain FV5069/pFV31 and transformants selected on LB agar (Lennox, 1955, Virology, 1:190)+50 µg/ml kanamycin. The strains obtained were named FV5069/pFV31/pND-D1 and FV5069/pFV31/pND-D2.

EXAMPLE 3
Formation of Pantothenate by Various Strains Derived from E. coli FV5069/pFV31

The quantitative determination of D-pantothenate took place by means of the Lactobacillus plantarum pantothenate assay (test strain: Lactobacillus plantarum ATCC 8014, cat. No. 3211-30-3; culture medium: Bacto pantothenate assay medium (DIFCO Laboratories, Michigan, USA), cat. No. 0604-15-3). This indicator strain can grow only in the presence of pantothenate in the indicated culture medium and displays a photometrically measurable, linear dependency of the growth on the concentration of pantothenate in the medium. The hemicalcium salt of pantothenate was used for the calibration (Sigma, product designation P 2250). The optical density was determined on an LKB Biochrom Photometer of the company Pharmacia Biotech (Freiburg, Germany) at a measuring wavelength of 580 nm (o.D.$_{580}$).

The production of pantothenate of the E. coli strains FV5069/pFV31, FV5069/pFV31/pND-D1 and FV5069/pFV31/pND-D2 was determined with glucose or saccharose as substrate. Medium E was used as test medium, which contained either 4 g/l glucose or 4 g/l saccharose as substrate and was supplemented in the case of strains FV5069/pFV31/pND-D1 and FV5069/pFV31/pND-D2 with 50 µg/ml kanamycin. 50 ml test medium present in a 500 ml Erlenmeyer flask were inoculated in such a manner, starting from a culture of the same medium 16 hours old, that the o.D.$_{580}$ was 0.1. After 72 hours incubation of these cultures at 37° C. and 250 rpm the cells were pelletized by a 10-minute centrifugation at 5000×g. The cell-free supernatant obtained was sterilized by filtration and stored until quantification of pantothenate at 4° C.

The quantification of the D-pantothenate in the culture supernatant took place by means of L. plantarum ATCC 8014 according to instructions of the manual of the company DIFCO (DIFCO MANUAL, 10$^{th}$ edition, pp. 1100–1102; Michigan, USA). The results of these measurements are shown in Table 3 and Table 4.

TABLE 3

Accumulation of pantothenate with glucose as substrate

| Strain | Gene | Pantothenate (µg/ml) |
|---|---|---|
| FV5069/pFV31 | — | 2 |
| FV5069/pFV31/pND-D1 | $panD_{E.c.}$ | 24 |
| FV5069/pFV31/pND-D2 | $panD_{C.g.}$ | 58 |

TABLE 4

Accumulation of pantothenate with saccharose as substrate

| Strain | Gene | Pantothenate (µg/ml) |
|---|---|---|
| FV5069/pFV31 | — | 2 |
| FV5069/pFV31/pND-D1 | $panD_{E.c.}$ | 47 |
| FV5069/pFV31/pND-D2 | $panD_{C.g.}$ | 69 |

Figure 1:
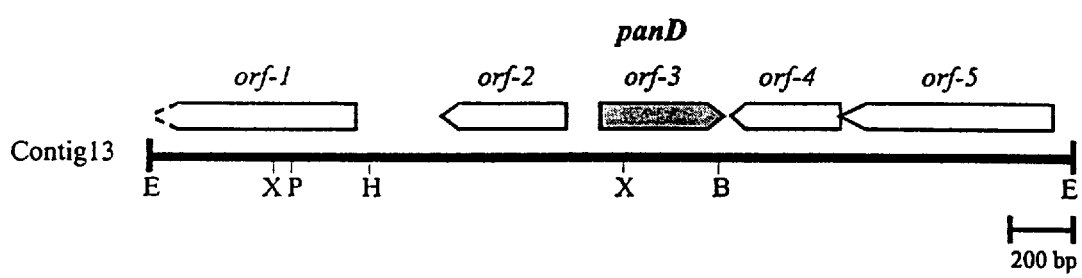
FIG. 1: Map of contig13 with orf1-orf5

The abbreviations used in the figures have the following significance:

T1T2: Transcription terminator of the rrnB gene
Ptac: tac promoter
panD: Coding range of the panD gene
rep-C.g.: DNA region for replication in C. glutamicum
oriV-E.c.: Origin for vegetative transfer in E. coli
kan: Resistance gene for kanamycin
EcoRI: Cleavage site of the restriction enzyme EcoRI
E: Cleavage site of the restriction enzyme EcoRI
BamHI: Cleavage site of the restriction enzyme BamHI
B: Cleavage site of the restriction enzyme BamHI
BglII: Cleavage site of the restriction enzyme BglII
ClaI: Cleavage site of the restriction enzyme ClaI H: Cleavage site of the restriction enzyme HindIII
P: Cleavage site of the restriction enzyme PstI
PstI: Cleavage site of the restriction enzyme PstI
SalI: Cleavage site of the restriction enzyme SalI ScaI: Cleavage site of the restriction enzyme ScaI
SphI: Cleavage site of the restriction enzyme SphI
X: Cleavage site of the restriction enzyme XbaI
XhoI: Cleavage site of the restriction enzyme XhoI

What is claimed is:

1. A method for the production of pantothenic acid comprising:

a) transforming a vector into an Enterobacteriaceae microorganism to produce a recombinant Enterobacteriaceae microorganism, wherein said vector comprises a panD gene operably linked to a suitable regulatory sequence;

b) growing said recombinant Enterobacteriaceae microorganism under conditions suitable for the production of pantothenic acid in an appropriate culture medium; and c) recovering said pantothenic acid from said culture medium;

wherein said Enterobacteriaceae microorganism comprises a plasmid pFV31 or pFV202, and wherein said panD gene encodes aspartate-1-decarboxylase and originates from Corynebacterium.

2. The method of claim 1, wherein said Enterobacteriaceae microorganism is *E. coli*.

Figure 2:
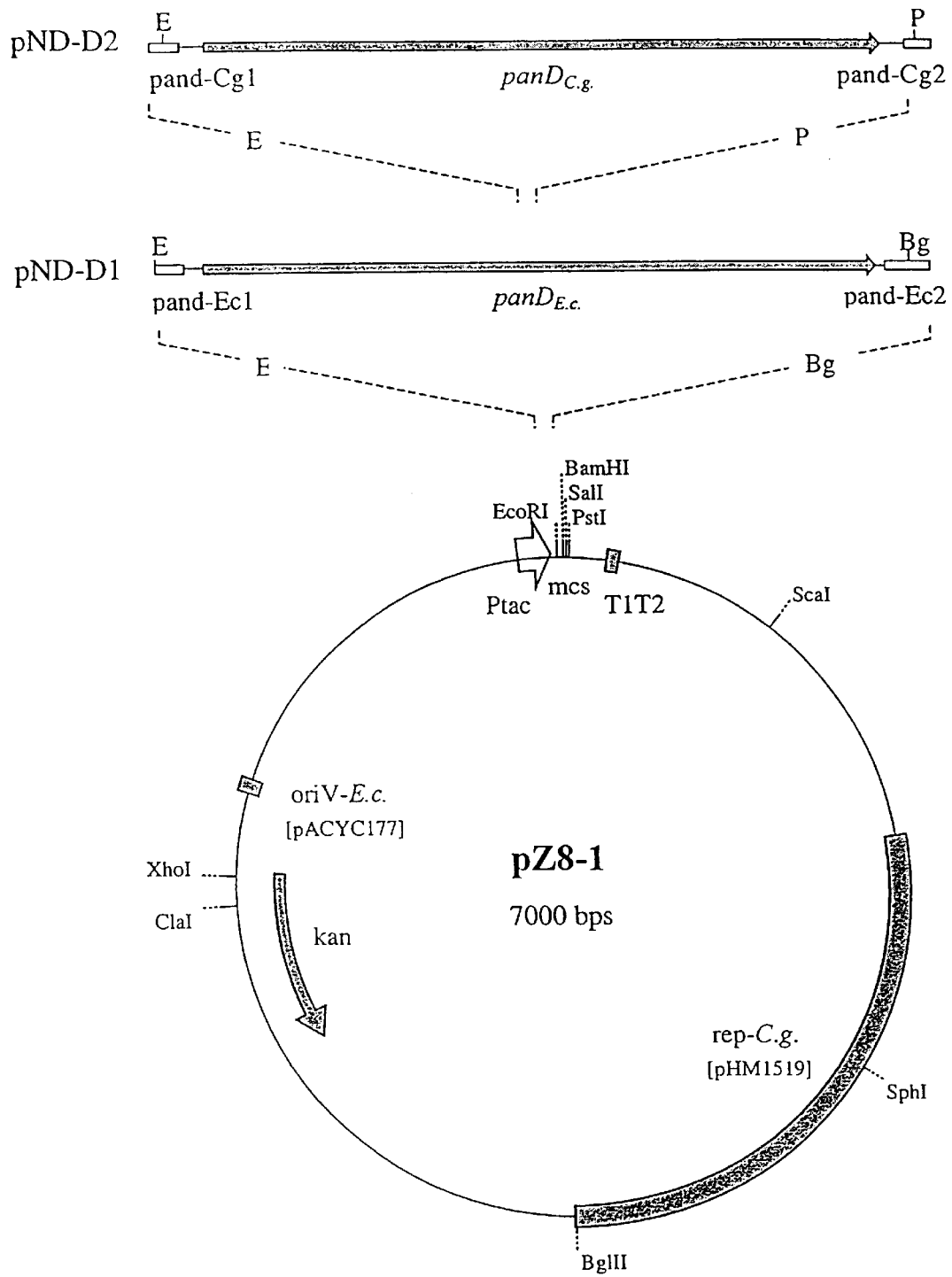
FIG. 2: Map of plasmid pZ8-1 and cloning strategy of plasmids pND-D1 and pND-D2

3. The method of claim 1, wherein said vector comprising a panD gene is pND-D2, which is characterized by the restriction map reproduced in FIG. 2 and deposited as *Corynebacterium glutamicum* ATCC13032/pND-D2 under the designation DSM 12438.

4. The method of claim 1, wherein said Enterobacteriaceae microorganism is *E. coli* and wherein said vector comprising a panD gene is pND-D2, which is characterized by the restriction map reproduced in FIG. 2 and deposited as *Corynebacterium glutamicum* ATCC13032/pND-D2 under the designation DSM 12438.

5. A microorganism of the species *E. coli* which contains the plasmid pFV31 and/or pFV202 and which is transformed with a vector comprising a nucleotide sequence encoding the panD gene product, which is aspartate-1-decarboxylase, whose amino acid sequence is set forth in SEQ ID NO:2.

* * * * *